(12) United States Patent
Ford, Jr.

(10) Patent No.: US 8,840,937 B2
(45) Date of Patent: Sep. 23, 2014

(54) COMPOSITION AND METHOD FOR RECOVERY FROM MILD TRAUMATIC BRAIN INJURY

(76) Inventor: Walter Joe Ford, Jr., Plano, TX (US)

( * ) Notice: Subject to any disclaimer, the term of this patent is extended or adjusted under 35 U.S.C. 154(b) by 69 days.

(21) Appl. No.: 13/408,689

(22) Filed: Feb. 29, 2012

(65) Prior Publication Data

US 2013/0224169 A1    Aug. 29, 2013

Related U.S. Application Data

(60) Provisional application No. 61/514,390, filed on Aug. 2, 2011.

(51) Int. Cl.
| | | |
|---|---|---|
| *A61K 36/00* | (2006.01) | |
| *A61K 36/16* | (2006.01) | |
| *A61K 36/28* | (2006.01) | |
| *A61K 36/906* | (2006.01) | |

(52) U.S. Cl.
USPC ........... 424/732; 424/752; 424/759; 424/764; 424/725

(58) Field of Classification Search
None
See application file for complete search history.

(56) References Cited

U.S. PATENT DOCUMENTS

| | | | |
|---|---|---|---|
| 2005/0202104 A1* | 9/2005 | Gianesello et al. | 424/725 |
| 2006/0062859 A1* | 3/2006 | Blum et al. | 424/725 |
| 2006/0239928 A1* | 10/2006 | Heit et al. | 424/45 |
| 2009/0068128 A1* | 3/2009 | Waddington | 424/59 |
| 2009/0175985 A1* | 7/2009 | Canham | 426/72 |
| 2009/0186127 A1* | 7/2009 | Krumhar et al. | 426/72 |
| 2011/0020443 A1* | 1/2011 | Liu et al. | 424/464 |
| 2012/0225053 A1* | 9/2012 | Dushenkov et al. | 424/94.65 |
| 2013/0064803 A1* | 3/2013 | Naidu et al. | 424/94.6 |

FOREIGN PATENT DOCUMENTS

WO    WO 00/57726    * 10/2000

* cited by examiner

*Primary Examiner* — Christ R Tate
(74) *Attorney, Agent, or Firm* — James R. Gourley; Carstens & Cahoon, LLP

(57) ABSTRACT

A method and composition for reducing the recovery time for a human suffering from mild traumatic brain injury are provided. The composition is a mixture of component supplements that synergistically address the symptoms of the condition and the damage done by the injury.

15 Claims, No Drawings

COMPOSITION AND METHOD FOR RECOVERY FROM MILD TRAUMATIC BRAIN INJURY

CROSS-REFERENCE TO RELATED APPLICATION

This application claims benefit of priority to U.S. Provisional Application No. 61/514,390 filed Aug. 2, 2011 entitled "Concussion Recovery Aid Formula."

BACKGROUND OF THE INVENTION

1. Technical Field

The present invention relates to a composition and method for reducing the recovery time for humans afflicted with mild traumatic brain injuries.

2. Description of Related Art

The injury to the human body commonly known as a "concussion" is also referred to by various other names, such as mild traumatic brain injury (MTBI), mild head injury, mild head trauma, and mild brain injury. The relevant medical literature has used the terms concussion and MTBI interchangeably in the past, but has recently begun to favor MTBI.

MTBI can occur any time a person's head is violently accelerated or decelerated, causing the brain to impact the skull. Common situations that may cause a violent acceleration or deceleration of a person's head include sporting activities, car accidents, acts of violence, or falling.

According to the U.S. National Institutes of Health, the symptoms of MTBI can range from mild to severe, and can include altered level of consciousness (drowsy, hard to arouse, or similar changes), loss of motor skills, confusion or not thinking straight, headache, loss of consciousness, memory loss (amnesia) of events before the injury or immediately after, nausea and vomiting, seeing flashing lights, or feelings of "lost time." The recovery period for someone suffering from MTBI can be days, weeks or months from the initial injury. During the recovery period, the patient may be withdrawn, easily upset, or confused, have difficulty with tasks that require memory or concentration, experience mild headaches, and show less tolerance for noise.

Treatment for MTBI offered by the prior art is typically rest and perhaps an analgesic for any symptomatic headaches that may occur. To date, the market has not provided a composition or method that reduces the recovery time for MTBI. Consequently, a need exists for a composition and method for shortening the recovery time for MTBI.

SUMMARY OF THE INVENTION

The proposed invention is a composition and method for reducing the recovery time for individuals suffering from MTBI. The inventive composition is a combination of vitamins, minerals, organic acids, botanical extracts and herbs that synergistically act to repair the damage caused by MTBI, and improve the areas of brain and body function most affected by MTBI.

In one embodiment, the composition comprises vitamin C, thiamine, riboflavin, niacin, vitamin B-6, folic acid, and vitamin B-12, biotin, magnesium, choline, feverfew extract, L-glutamine, L-tyrosine, acetyl L-carnitine, gamma-aminobutyric acid (GABA), N,N-dimethylglycine (DMG), ginkgo biloba, para-aminobenzoic acid (PABA), dimethylaminoethanol (DMAE), alpha lipoic acid, bromelain, bilberry extract, L-theanine, guarana extract, huperzine A, and turmeric extract. In another embodiment, the composition consists essentially of these ingredients. In another embodiment, the composition further comprises docosahexaenoic acid (DHA).

Other aspects, embodiments and features of the invention will become apparent from the following detailed description of the invention. All patent applications and patents incorporated herein by reference are incorporated by reference in their entirety. In case of conflict, the present specification, including definitions, will control.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments.

DETAILED DESCRIPTION

The present invention is directed to a composition and method for reducing the recovery time for humans suffering from MTBI. The composition comprises a mixture of vitamins, minerals, organic acids, botanical extracts and herbs that synergistically act to repair the damage caused by MTBI, improve the areas of brain and body function most affected by MTBI, and generally alleviate the symptoms of MTBI.

In one embodiment, the composition comprises vitamin C, thiamine, riboflavin, niacin, vitamin B-6, folic acid, and vitamin B-12, biotin, magnesium, choline, feverfew extract, L-glutamine, L-tyrosine, acetyl L-carnitine, gamma-aminobutyric acid (GABA), N,N-dimethylglycine (DMG), ginkgo biloba, para-aminobenzoic acid (PABA), dimethylaminoethanol (DMAE), alpha lipoic acid, bromelain, bilberry extract, L-theanine, guarana extract, huperzine A, and turmeric extract. All of the components of the inventive composition are available individually from commercial suppliers, but have never been combined into a single composition, and have never been suggested to be combined in the manner claimed. In another embodiment, the composition consists essentially of these ingredients. A composition consists essentially of these ingredients when no or substantially no other active ingredients are included. Ingredients not considered active ingredients include those that are included solely for palatability, flow agents, or other ingredients not meant to address any symptoms of MTBI.

As described in detail below, some of these compounds act as anti-inflammatories, some are involved in neurotransmitter synthesis or protection, and others generally assist the body in repairing damage done by MTBI. Through clinical trials, Applicant herein has discovered that the inventive composition described below cut the recovery time in patients suffering from MTBI in half. This composition represents an advancement in the art because previously, a patient with MTBI was told to rest and perhaps take an analgesic for headaches. Cutting the recovery time in half has special implications for people who engage in sport and desire to return to competition as quickly as possible, but the composition described herein can help anyone suffering from MTBI to recover more quickly.

One of the components of the inventive composition is vitamin C. Vitamin C is a powerful antioxidant that the human body uses to help repair tissues and blood vessels. Preferably, the vitamin C used in the inventive composition is in the form of ascorbic acid. Another component is thiamine (also known as vitamin B1). Thiamine is used by the human body in the synthesis of neurotransmitter acetylcholine and gamma-aminobutyric acid (GABA).

Riboflavin, also known as vitamin B2, is another component of the inventive composition. It, along with the other B-vitamins Niacin, vitamin B-6, folic acid, and vitamin B-12, are important co-factors in energy production and red blood cell health. Red blood cells transport oxygen throughout the body, including the brain. In a preferred embodiment, niacin is provided in the form of niacinamide, vitamin B6 in the form of pyridoxal-5-phosphate, and vitamin B-12 in the form of cyanocobalamin.

Biotin (vitamin B-7) is included because it is crucial to nerve tissue health, and can help any nerves damaged by MTBI to recover more quickly. Magnesium is another component of the inventive composition that is crucial to nerve tissue and neuron health. A decrease in magnesium can lead to an increase in neuro-excitotoxic degeneration. Magnesium also helps maintain proper blood glucose levels, which directly affects serotonin levels in the brain. In a preferred embodiment, magnesium is provided in the form of magnesium glycyl glutamine chelate. Magnesium glycyl glutamine chelate will also provide the inventive composition with L-glutamine, which is a special form of glutamine that passes through the blood brain barrier. L-glutamine helps stabilize other minerals and reduce acidosis that can occur when the body is under stress.

Choline, another component of the inventive composition, is a precursor for acetylcholine, which is a neurotransmitter that assists in focus and concentration. Choline is also used in construction of cell membranes, and as an anti-inflammatory. Another anti-inflammatory used in the inventive composition feverfew extract (preferably feverfew leaf extract). It is particularly useful for treatment of headaches, including migraine headaches.

Another component of the inventive composition is L-tyrosine, which assists in production of neurotransmitters L-dopa, dopamine, norepinepherine, epinepherine. These neurotransmitters are important factors in the brain's recovery from MTBI.

Acetyl L-carnitine, another component, is a powerful antioxidant that can cross the blood-brain barrier, helping to normalize brain blood flow and protect brain cells from deterioration. Gamma-aminobutyric acid (GABA) regulates neuronal excitability. GABA's activity can have the effect of slowing or halting the neuro-excitotoxic cascade that can occur as a result of MTBI. Dimethylglycine (DMG) is a powerful methyl donor that decreases free radical activity in degenerative conditions. DMG also assists in production of all neurotransmitters.

Ginkgo Biloba leaf extract has been shown to increase brain blood flow, improve memory function and help reduce the experience of vertigo. 4-Aminobenzoic acid (also known as para-aminobenzoic acid or PABA) is a powerful anti-oxidant. PABA prevents cross-binding caused by free-radical formation after the MTBI trauma, and helps with cell membrane fluidity. Dimethylaminoethanol (DMAE) is a precursor to the neurotransmitter acetylcholine. DMAE can help restore and increase short term memory, improve rapid eye movement (REM) sleep, increase focus, improve overall brain power.

Alpha lipoic acid (ALA) improves nerve transmission and helps regenerate nerve tissue. ALA also serves as a protective against glycation and oxidation during stress, and protects mitochondrial function. ALA can also help decrease accumulation of tau proteins, which have been found in high levels in the fluid surrounding the brain after head trauma. L-theanine is an amino acid that decreases neuroexcitotoxicity, which leads to neuron destruction and tau protein build up due to glutamic acid. It also increases alpha brain wave activity.

Bromelain is a botanical extract (typically extracted from the stems of pineapples) proteolytic enzyme mixture that reduces inflammation in tissues after trauma or sports injury. Bromelain also reduces edema by stabilizing vascular permeability. As an enzyme, it can be measured in milk clotting units (MCU) which are based on how fast one gram of the enzyme will digest milk proteins.

Bilberry extract (preferably bilberry fruit extract) contains anthocyanidins, and helps decrease vascular fragility, stabilize cell membrane permeability, and improve optic nerve function by decreasing inflammation. Extract of the guarana plant (preferably of the guarana seed) increases memory and mental alertness, and improves mood. Huperzine A is a botanical extract that protects nerves, improves memory, and assists in production of neurotransmitters. A method of synthesizing huperzine A has also been developed. Extract of turmeric rhizomes contains high levels of curcuminoids, especially curcumin. Tumeric extract acts as an anti-inflammatory, a neuroprotective, and protects against DNA damage due to stress.

In one embodiment of the present invention docosahexaenoic acid (DHA) is also included as a component in the composition. DHA can be found in many different nutritional supplement products, but is most preferably found in fish oil. DHA is an omega-3 fatty acid, and is a primary component of the human brain. It is included in one embodiment of the inventive composition to decrease the brain's inflammatory response, and contribute to neuron cell membrane health. Because fish oil cannot be included in a powdered composition, it is preferably provided to the MTBI-suffering patient as a separate capsule. In a most preferred embodiment, it is administered at a dosage of 1000 mg per dose.

In one embodiment, the components listed above are included in a composition in an effective amount that reduces the recovery time for a human suffering from MTBI. Each component should also be administered at levels that are not toxic to the consumer.

Although not limiting the invention in its broadest sense, Applicant herein has determined one example of a composition that contains the components described above at effective amounts, when administered twice per day, to reduce the recovery time for a human suffering from MTBI. The table below lists one example of the weight of each component included in one serving of the inventive composition described above.

TABLE 1

Example Serving of Inventive Composition

| Component | Amount |
|---|---|
| Vitamin C (as Ascorbic Acid) | 250 mg |
| Thiamine | 5 mg |
| Riboflavin | 5 mg |
| Niacin (as Niacinamide) | 5 mg |
| Vitamin B-6 (pyridoxal-5-phosphate) | 20 mg |
| Folic Acid | 0.1 mg |
| Vitamin B-12 (cyanocobalamin) | 0.05 mg |
| Biotin | 0.5 mg |
| Magnesium | 265 mg |
| Choline (Bitartrate) | 1500 mg |
| Feverfew leaf Extract (std. to 0.4% parthenolides) | 60 mg |
| L-Glutamine | 1500 mg |
| L-Tyrosine | 100 mg |
| Acetyl L-Carnitine | 1000 mg |

TABLE 1-continued

Example Serving of Inventive Composition

| Component | Amount |
|---|---|
| GABA (gamma amino butyric acid) | 2 mg |
| N,N-Dimethylglycine (DMG) | 500 mg |
| *Ginkgo biloba* Leaf Extract (std. to 24% ginkgo flavones glycosides) | 150 mg |
| PABA (para-amino benzoic acid) | 50 mg |
| DMAE L-Bitartrate | 50 mg |
| Alpha Lipoic Acid | 100 mg |
| Bilberry Fruit Extract (*Vaccinium myrtillus L.*) (std. to contain 20 mg anthocyanidins) | 80 mg |
| L-Theanine (Suntheanine ®) | 50 mg |
| Guarana Seed Extract | 50 mg |
| Huperzine | 0.01 mg |
| Turmeric (Rhizome) | 50 mg |
| Bromelain | 5000 MCU |

Clinical trials were run by Applicant using the composition in the table above plus 1000 mg of DHA-rich fish oil in a separate capsule. The composition was initially in powder form and mixed with water or fruit juice shortly before consumption, except the fish oil capsule which was swallowed whole. Applicant found that those individuals who did take the supplement twice per day for seven days recovered from MTBI, on average, in about 2.25 days. By contrast, those individuals who did not take the supplement recovered from MTBI, on average, in about 4.5 days. The inventive composition was successful in cutting the recovery time by about half. Recovery time was determined based on each individual's response to the Rivermead Post Concussion Symptoms Questionnaire (See Potter S, Leigh E, Wade D, Fleminger S (December 2006). "The Rivermead Post Concussion Symptoms Questionnaire: A confirmatory factor analysis". J. Neurol. 253 (12): 1603-14) and the individual's performance on reflex testing software. The reflex testing software displayed a grid of squares, and measured the amount of time it took the user to press each square after it was highlighted by the software program. After six runs for each individual, the highest and lowest times were thrown out, and the remaining four were averaged.

One embodiment of the invention is a method of reducing the recovery time in a human suffering from MTBI comprising the steps of: administering to said human an effective amount of the inventive composition described above at least once per day, until said human has recovered from MTBI. In a preferred embodiment, the total amount of each component of the composition administered per day is approximately the value found in Table 1 above. In a most preferred embodiment, the inventive composition is administered twice per day.

In another preferred embodiment, the inventive composition is a powdered mixture of its various components, which can be mixed with water, other aqueous beverage such as a fruit juice, or food product, prior to consumption. In another embodiment, the inventive composition is in capsule form, time-release capsule form, pill form, or a mixture of powder and capsules or pills. Providing the composition in capsule or pill form may make compliance with a treatment regimen difficult due to the large number of capsules or pills that would need to be consumed.

It will now be evident to those skilled in the art that there has been described herein a composition and method that can be used to reduce the recovery time for an individual suffering from MTBI. Although the invention hereof has been described by way of a preferred embodiment, it will be evident that other adaptations and modifications can be employed without departing from the spirit and scope thereof. The terms and expressions employed herein have been used as terms of description and not of limitation; and thus, there is no intent of excluding equivalents, but on the contrary it is intended to cover any and all equivalents that may be employed without departing from the spirit and scope of the invention.

In sum, while this invention has been particularly shown and described with reference to a preferred embodiment, it will be understood by those skilled in the art that various changes, in form and detail may be made therein without departing from the spirit and scope of the invention.

What is claimed is:

1. A mild traumatic brain injury (MTBI) recovery composition comprising the following ingredients:
    vitamin C, thiamine, riboflavin, niacin, vitamin B-6, folic acid, and vitamin B-12, biotin, magnesium, choline, feverfew extract, L-glutamine, L-tyrosine, acetyl L-carnitine, gamma-aminobutyric acid (GABA), dimethylglycine (DMG), ginkgo biloba, para-aminobenzoic acid (PABA), dimethylaminoethanol (DMAE), alpha lipoic acid, bromelain, bilberry extract, L-theanine, guarana extract, huperzine A, and turmeric extract, wherein said ingredients are provided in the following amounts per serving:
    250 mg Vitamin C;
    5 mg Thiamine;
    5 mg Riboflavin;
    5 mg Niacin;
    20 mg Vitamin B-6;
    0.1 mg Folic Acid;
    0.05 mg Vitamin B-12;
    0.5 mg Biotin;
    265 mg Magnesium;
    1500 mg Choline;
    60 mg Feverfew Extract;
    1500 mg L-Glutamine;
    100 mg L-Tyrosine;
    1000 mg Acetyl L-Carnitine;
    2 mg GABA;
    500 mg DMG;
    150 mg Ginkgo Biloba Extract;
    50 mg PABA;
    50 mg DMAE;
    100 mg Alpha Lipoic Acid;
    80 mg Bilberry Extract;
    50 mg L-Theanine;
    50 mg Guarana Extract;
    0.01 mg Huperzine A;
    50 mg Turmeric; and
    5000 milk clotting units Bromelain.

2. The composition of claim 1 further comprising magnesium glycyl glutamine chelate.

3. The composition of claim 1 further comprising niacinamide.

4. The composition of claim 1 further comprising pyridoxal-5-phosphate.

5. The composition of claim 1 wherein said vitamin B-12 is provided in the form of cyanocobalamin.

6. The composition of claim 1 consisting essentially of said ingredients.

7. The composition of claim 1 wherein said bilberry extract comprises bilberry fruit extract.

8. The composition of claim 1 wherein said guarana extract comprises guarana seed extract.

9. The composition of claim 1 wherein said feverfew extract comprises feverfew leaf extract.

10. The composition of claim 1 wherein said ingredients further comprise docosahexaenoic acid (DHA).

11. The composition of claim 10 wherein said DHA is provided by fish oil.

12. A method of reducing recovery time for a human suffering from MTBI comprising:
   administering an effective amount of a composition comprising effective amounts of each of the following ingredients: vitamin C, thiamine, riboflavin, niacin, vitamin B-6, folic acid, and vitamin B-12, biotin, magnesium, choline, feverfew extract, L-glutamine, L-tyrosine, acetyl L-carnitine, gamma-aminobutyric acid (GABA), dimethylglycine (DMG), ginkgo biloba, para-aminobenzoic acid (PABA), dimethylaminoethanol (DMAE), alpha lipoic acid, bromelain, bilberry extract, L-theanine, guarana extract, huperzine A, and turmeric extract to said human at least once per day.

13. The method of claim 12 wherein said administering occurs at least twice per day.

14. The method of claim 12 wherein said composition is in powdered form and is mixed with an aqueous beverage prior to said administration.

15. The method of claim 13 wherein said composition comprises the composition according to claim 1.

* * * * *